United States Patent [19]
Koutrakis et al.

[11] Patent Number: 5,302,191
[45] Date of Patent: Apr. 12, 1994

[54] DENUDER FOR GAS SAMPLING

[75] Inventors: Petros Koutrakis, Wellesley; Stephen T. Ferguson, W. Concord; Jack M. Wolfson, Jamaica Plain, all of Mass.

[73] Assignee: President and Fellows of Harvard College, Cambridge, Mass.

[21] Appl. No.: 938,854

[22] Filed: Sep. 1, 1992

[51] Int. Cl.$^5$ ............................................ B01D 46/24
[52] U.S. Cl. ........................................ 95/285; 55/270; 55/485; 55/486; 55/523; 55/524
[58] Field of Search ............... 55/52, 97, 270, 485, 55/486, 523, 524, 528

[56] References Cited
U.S. PATENT DOCUMENTS

| | | | |
|---|---|---|---|
| 4,133,202 | 1/1979 | Marple | 55/270 X |
| 4,347,912 | 9/1982 | Flocke et al. | 55/524 X |
| 4,643,749 | 2/1987 | Miura | 55/523 |
| 4,902,314 | 2/1990 | Mizukami et al. | 55/97 |
| 4,902,318 | 2/1990 | Stevens et al. | 55/270 |
| 4,961,966 | 10/1990 | Stevens et al. | |
| 4,983,434 | 1/1991 | Sassa | 55/528 X |

OTHER PUBLICATIONS

Koutrakis et al., 22(1), *Atmospheric Environment*, 157, 1988.
Koutrakis et al., 26A, *Atmospheric Environment*, 987, 1992.
Koutrakis et al., 22, *Environmental Science & Technology*, 1463, 1988.
Koutrakis et al., 12, *Aerosol Science and Technology*, 607, 1990.
Hering, "Air Sampling Instruments", 7th edition, (1989), American Conference of Governmental Industrial Hygienists, Cincinnati, Ohio.

*Primary Examiner*—Charles Hart
*Attorney, Agent, or Firm*—Lyon & Lyon

[57] ABSTRACT

A denuder for collection of gases, consisting of a plurality of generally parallel elongated tubes having a surface formed from an inert non-metallic material, said tubes being configured and arranged to allow recovery of gaseous material collected on each said surface.

19 Claims, 4 Drawing Sheets

DENUDER FOR GAS SAMPLING

BACKGROUND OF THE INVENTION

This invention relates to apparatus and methods for sampling atmospheric gases and particles.

During the last decade, diffusion denuders have been used in a variety of atmospheric monitoring studies to collect gaseous atmospheric pollutants (Durham et al., 12 *Atmospheric Environment* 883 (1978); Ferm, 13 *Atmospheric Environment* 1385 (1979); Shaw et al., 16 *Atmospheric Environment* 845 (1982); Forest et al., 16 *Atmospheric Environment* 1473 (1982); Braman et al., 54 *Analytical Chemistry* 356 (1982)). In these studies, glass or metallic hollow tubes were coated to selectively collect the different gases while allowing other gases and particles to penetrate. These tubular denuders allow high collection efficiencies only for low collection flow rates (less than 1 liter/minute). In 1983, Possanzini et al. developed the annular denuder which efficiently collects atmospheric gas at higher flow rates (higher than 10 liters/minute). Koutrakis et al., 22(1) *Atmospheric Environment* 157 (1988b) presented an improved method for measuring strong acidity of atmospheric aerosols using an $NH_3$ diffusion denuder. The denuder was constructed using a foil laminate honeycomb consisting of hexagonal cells of size 0.635 cm, and length 5.08 cm.

Use of a series of two annular denuders (coated with sodium carbonate and citric acid, respectively) makes possible the collection of acidic gases, such as $SO_2$, $HNO_3$, $HNO_2$, gas phase organic acids, and basic gases, such as $NH_3$. The use of a filter pack downstream from the annular denuders allows the simultaneous collection of particles. This simultaneous collection of particles and gases is feasible only for high flow rates since, for collection flow rates less than 1 liter/minute, the collected particulate matter is not usually enough for analysis unless multiday samples are collected. This is not generally desired for atmospheric chemistry studies where a fine resolution of concentration profiles is necessary to understand processes affecting the origin and fate of atmospheric pollutants. A glass impactor which can be placed upstream from the denuder/filter pack system is useful for removal of coarse particles from the air sample. This inlet is preferably inert, so that losses of reactive gases such as nitric acid, sulphur dioxide, and nitrous acid are negligible.

Denuder/filter pack systems are cost effective because they allow simultaneous sampling of gases and particles using the same pumping system, which can be the most expensive part of the sampling unit. Use of a denuder is also necessary to prohibit reactions between gases and collected particles on the filter media. For example, a significant portion of particulate acidity can be neutralized on the Teflon filter by ammonia. Therefore, a citric acid-coated denuder is used upstream from the filter to remove ammonia from the air sample. An ozone denuder can be used upstream from the Teflon filter to prohibit interactions between ozone and the collected organic particulate matter. The coating of such a denuder is a mixture of nitrite and carbonate salts.

The partition coefficient of different atmospheric species between the particle and gaseous phase can be determined by using denuder/filter pack systems. Sampling of atmospheric semi-volatile compounds remains a challenge and is often inappropriately addressed by atmospheric chemists. For instance, collection of polyaromatic hydrocarbons (PAH) or ammonium nitrate is done using two stage filter packs. In the case of polyaromatic hydrocarbons, the first stage of filter pack is a Teflon filter to collect the particulate PAH, and the second stage is a sorbent (XAD-2 or Tenax) to collect the gas phase PAH. However, the sorbent will collect PAHs which were originally sampled by the Teflon filter, and were later volatilized. With an appropriately coated denuder, the amount of the semi-volatile PAH originally in the gas phase can be determined.

Sampling of ammonium nitrate can also be a problem. Filter pack techniques use a Teflon filter to collect particles and a nylon filter (or a sodium carbonate-coated glass fiber filter) to collect nitrates (in nitric acid form) downstream from the Teflon filter. However, the nitrate on the second filter can originate from vapor phase nitric acid or from the volatilization of ammonium nitrate collected on the Teflon filter. Therefore, it is difficult or impossible to determine ammonium nitrate concentrations unless a nitric acid denuder is used upstream from the filter pack. In addition, the volatilization of nitrate from the Teflon filter can be associated with two different processes: (a) the dissociation of ammonium nitrate:

$$NH_4NO_3(p) \longrightarrow NH_3(g) + HNO_3(g),$$

and (b) the neutralization of acid aerosol sulfate by ammonium nitrate:

$$NH_4NO_3(p) + H^+ (p)[NH_4HSO_4, (NH_4)_3H(SO)_2,$$

or $$H_2SO_4] \longrightarrow$$

$$NH_4^+ (p)[NH_4)_2SO_4, NH_4HSO_4, (NH_4)_3H(SO_4)_2] + HNO_3(g).$$

The relative importance of these two mechanisms can be determined using a denuder/filter pack system (Koutrakis, et al., Submitted for publication to *Atmospheric Environment* (1992)). Denuders are used to remove nitric acid and ammonia from the air sample. The filter pack contains three filters: a Teflon filter to collect fine particles, a sodium carbonate-coated glass fiber filter to collect nitrate (which can originate from both ammonium nitrate dissociation and acid sulfate neutralization reaction, as shown in the above reactions), and a citric acid-coated glass fiber filter to collect ammonium (which originates form the dissociation of ammonium nitrate). By subtracting the number of ammonium moles collected on the third filter from the number of moles of nitrate collected on the second filter, it is possible to calculate the amount of lost particulate acidity from the Teflon filter.

The annular denuder/filter pack technology has made possible a number of field and laboratory studies which have enhanced understanding of the physical chemistry of inorganic atmospheric pollutants. However, this technology is relatively expensive (approximately $1500 per sampling unit) and time-consuming to use. In fact, coating and extraction of denuders requires skilled laboratory technicians and is labor intensive. The denuder preparation, extraction, and analysis costs are between $200 and $300. Also, shipping of the large units is expensive.

Koutrakis, et al., 26A *Atmospheric Environment* 987 (1992) (which is not admitted to be prior art to the present application) describe a filter pack for use with annular denuder technology. The annular denuder system used is the Harvard system in which a first denuder is coated with sodium bicarbonate and glycerol, and a second denuder is coated with citric acid and glycerol.

Koutrakis, et al., 22 *Environmental Science and Technology* 1463 (1988) describe an annular denuder/filter pack system for collection of acidic aerosols and gases. The sampler contains a glass impactor in combination with an annular denuder and filter pack system. The impactor plate is a porous glass disc impregnated with mineral oil. Two annular denuders are provided in series, the first of which is coated with sodium carbonate and glycerol to collect $SO_2$, $HNO_3$, and $HNO_2$. The second denuder is coated in the same way to measure any artifact nitrate and nitrite for correction of the $HNO_3$ and $HNO_2$ concentration.

Koutrakis, et al., 22 *Atmospheric Environment* 157 (1988) describe a method for measuring acidity of atmospheric aerosols by use of an ammonia diffusion denuder. A Harvard impactor was used to collect aerosol particles with aerodynamic diameter below 2.5 microns.

Koutrakis, et al., 12 *Aerosol Science and Technology* 607 (1990) describe a glass impactor for an annular denuder filter pack system in which a removable porous glass disc is impregnated with mineral oil. Stevens, et al. U.S. Pat. Nos. 4,902,318 and 4,961,966 describe an inlet apparatus for gas aerosol sampling having an elutriator column and an impactor section. The column is provided with a coating of a polytetrafluoroethylene-containing polymer.

Hering, "Air Sampling Instruments" (1989), describes a single stage impactor with ten circular jets in which the impactor surface is an oil-coated porous stainless steel plate.

SUMMARY OF THE INVENTION

Currently available annular denuder/filter pack technology has been extremely useful for atmospheric studies, but has a relatively high cost for both instrumentation and operation. Applicant has developed an alternative system which maintains and improves operational features, while significantly lowering the cost.

The system has a denuder component which replaces an annular denuder, (i.e., one composed of an outer glass tube with a closed glass cylinder inside), with a large number of small hexagonal glass tubes sealed inside an outer glass tube. The new system has the following advantages: 1) both the initial cost and the labor required for processing are much less; 2) a length of only about 3.8 cm yields the same collection capability as a length of 15 cm for the annular denuder, allowing a much more durable system; 3) this length also allows the use of several more denuders for simultaneous collection of a greater variety of gases; and 4) this new system is more convenient for large-scale monitoring studies.

In addition, an inlet is used which further reduces both the size and the cost. It has a multijet impactor with a size cut-off of 2.1 μm. All surfaces that are exposed to the sample air before the two denuders are coated with Teflon to minimize losses or reactive gases such as nitric acid. The new system also has a filter pack which costs less than those currently used, because it is manufactured by molding rather than machining the inert plastic parts.

This system costs at least three times less than existing annular denuder/filter pack systems and provides measurements equivalent to the annular denuder/filter pack system. Also, the denuder coating costs are significantly lower. The new system is considerably smaller than the annular denuder system and can be easily used for large field studies (with lower shipping and field operation costs).

This invention features a denuder adapted for accurate assessment of particles and gases present in a gas sample. A denuder is a tubular system with coated walls which trap specific gases, while allowing fine particles to pass through without significant loss. The design of such denuders allows reproduction in a compact form, and use in conjunction with impactor plates and filter packs for a complete and accurate assessment of pollutant gases and fine particles. Unlike some prior denuders, the gases collected on the surface of the denuder can be recovered.

Thus, in the first aspect, the invention features a denuder for collection of gases which includes a plurality of generally parallel elongated tubes having a surface formed from an inert non-metallic material, and is configured and arranged to allow recovery of gaseous material collected on the surface of the tubes.

In preferred embodiments, the non-metallic material is glass, or ceramic, or a plastic (such as a resin), and at least 20, 50, or 100 or more such elongated tubes are provided in the denuder. Most preferably, the tubes have a generally hexagonal cross-section so that the tubes can be fitted together with minimal loss of space within the denuder shell. It is preferred not to use tubes of circular cross-section in which a large amount of space within the denuder is lost from the contact areas between the outside of each such tube. Denuders of this invention provide a high surface to volume ratio, and thus can be used to make compact air samplers which can be readily placed within a sampler housing. The small elongated tubes can generally be formed from glass extruded inside an oven at high temperatures. The smaller tubes are sealed inside the larger tube by further extrusion of the combination of small tubes inside the large tube, again, inside an oven at high temperature. Alternatively, epoxy resins or ceramic glazes are used to seal the small tubes inside the large tube.

In other preferred embodiments, the denuder has a length of less than 5 cm, and a width of less than 6 cm, and is preferably combined with a gas inlet nozzle configured and arranged to allow gas to enter a gas collection system, and pass through the denuder to an impactor plate configured and arranged to collect particles in the gas.

In other embodiments, the nozzle impactor plate is configured and arranged to cause particles of size greater than 2.1 microns to contact the impactor plate, thereby being removed from the air stream, and the nozzle is provided with a circular array of apertures. Most preferably, the gas collection system has a plurality of denuders with at least one adapted to collect acid gases, and another adapted to collect basic gases; and a filter pack is provided and configured and arranged to collect particles not collected by the impactor plate. Such a filter pack may include one Teflon filter and additional coated glass fiber filters to collect acid or basic gases.

In another aspect, the invention features an arrangement whereby the series of denuders precedes the impactor stage, so that there is a greater minimization of losses of reactive gases on inlet surfaces prior to collection on the denuders.

In another aspect, the invention features a method for collection of gases by use of a denuder or gas collection system as described above.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

Figure 1A:
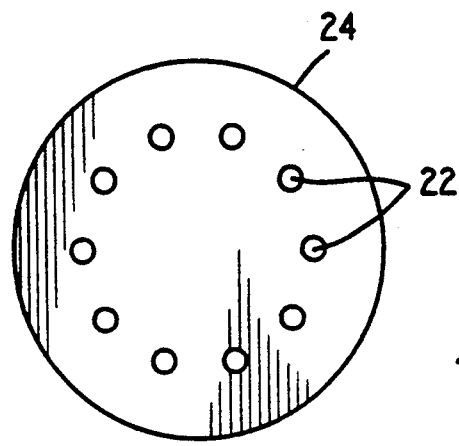
Figure 1B:
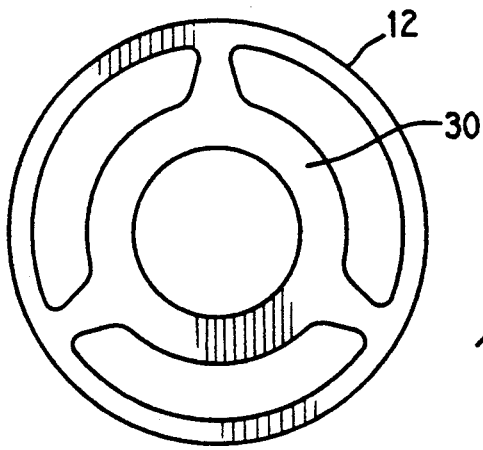
Figure 1C:
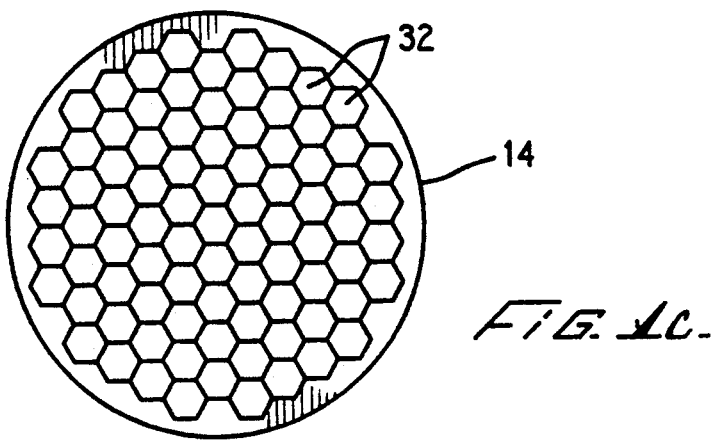
Figure 1D:
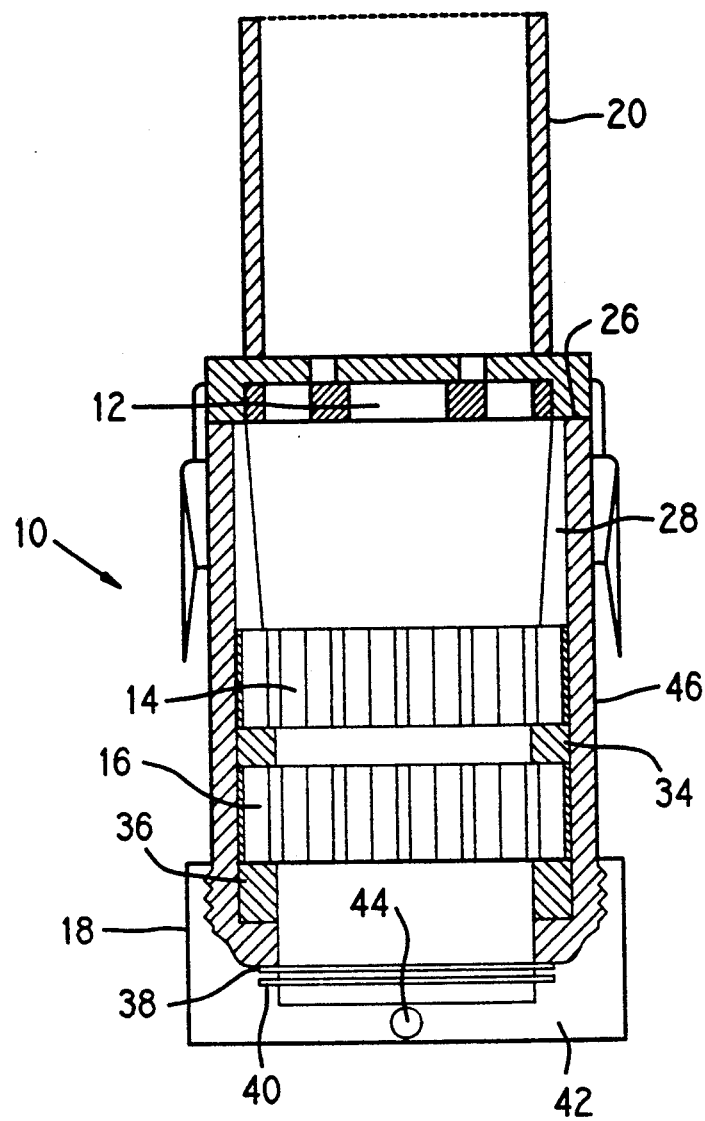

FIGS. 1A-D are diagrams of the annular denuder/filter pack system: FIG. 1D is a longitudinal sectional view of a system with two denuders, including a cross sectional view of the jets; FIG. 1A shows the jet layout; FIG. 1B shows the impactor plate; FIG. 1C shows the honeycomb denuder.

Figure 2:
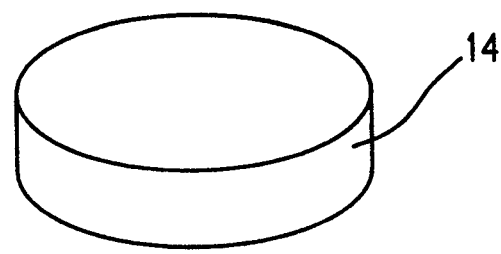
Figure 3:
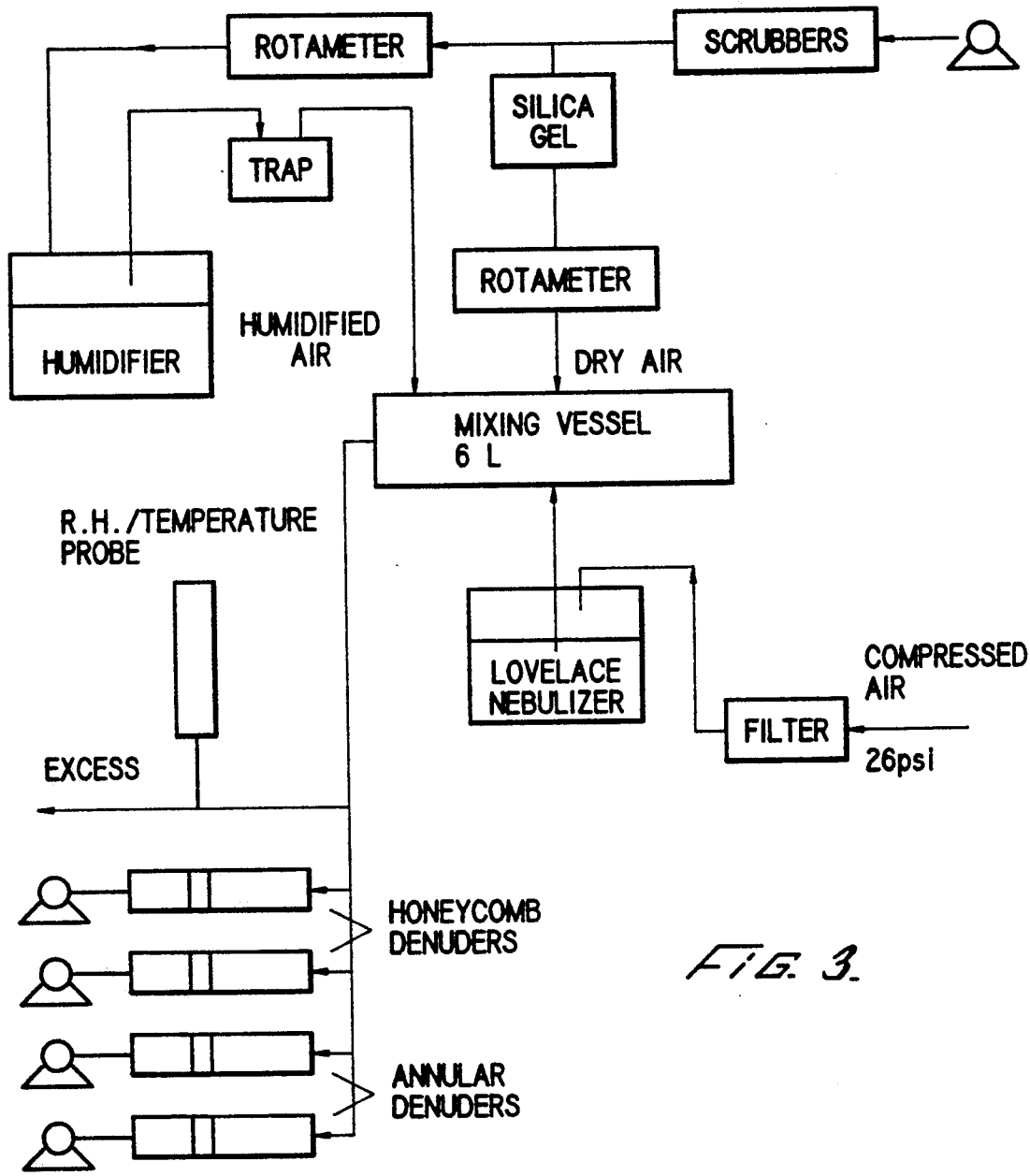
Figure 4:
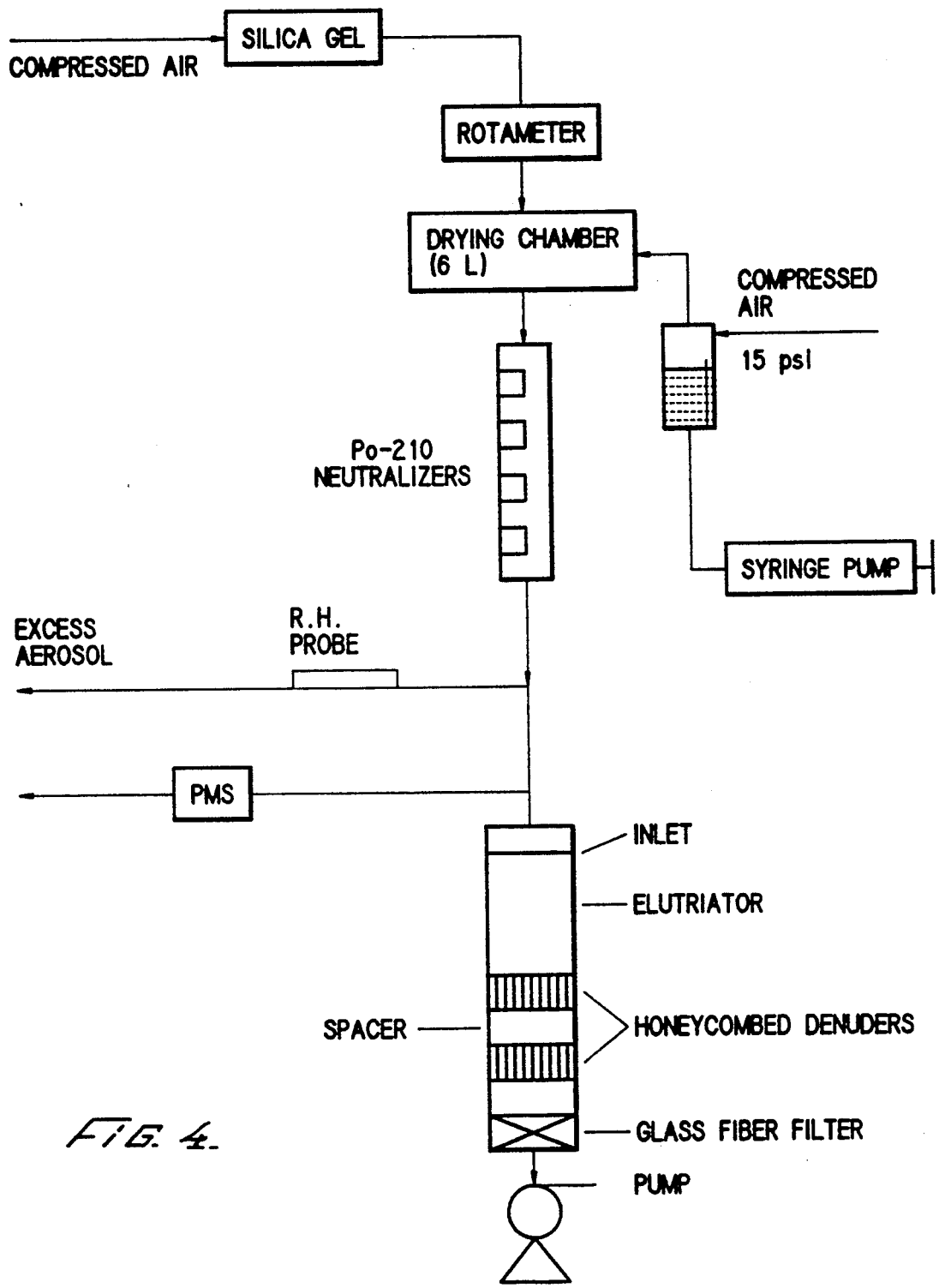

FIG. 2 is an isometric representation of a honeycomb denuder of height about 3.8 cm; and FIGS. 3 and 4 are schematic diagrams of gas test systems.

STRUCTURE

Referring to FIGS. 1A-D and 2, a honeycomb denuder/filter pack system 10, has three important features: an impactor 12 to remove coarse particles ($d_p$2.1 $\mu$m) from the air sample; two glass honeycomb denuders 14, 16 (the first removes acid gases, such as nitric acid, sulfur dioxide and nitrous acid; the second removes basic gases, such as ammonia); and a two stage filter pack 18 to collect fine particles.

Inlet 20 has a short elutriator to help exclude the largest particles from entering the sampler when the inlet is pointed downwards. Sample air is accelerated through the circular array of nozzles 22 in a jet layout 24, which causes particles larger than 2.1 $\mu$m to impact on impactor plate 12. This plate is a ring 30 of sintered stainless steel, coated with mineral oil, mounted in a ring 26 to hold it below nozzles 22. Below impactor plate 12 is a transition section 28 which allows sample air to flow smoothly around and through the impactor plate ring and to subsequently have practically uniform flow through the individual honeycomb tubes 32 of first denuder 14. All surfaces that are exposed to the sample air before the two denuders are coated with Teflon to minimize losses of reactive gases such as nitric acid.

Following transition section 28 is first honeycomb denuder 14 which is coated with sodium carbonate and glycerol to collect acid gases. Between the first and second denuders is an inert polyethylene spacer 34, which keeps the two denuders from exchanging coating material and allows the gas to pass from the first to the second denuder stage. The second honeycomb denuder is coated with citric acid and glycerol to collect basic gases. It is held in place by a stainless steel spring 36, which keeps transition section 28, denuders 14 and 16 and spacer 34 tightly held together, and thus assures that the sample air passes through the system properly. Below spring 36 is the two stage filter pack 18. A first filter 38 is made of Teflon, and collects the fine particles which were not collected on the impactor stage. Following the Teflon filter is a sodium carbonate-coated glass fiber filter 40, which collects acid gases produced from the reaction of acidic fine particles with particulate ammonium. At the very bottom is a filter pack holder 42, with a hose connection outlet 44 which connects to the sample pump tubing.

Sampler 10 has three basic parts which are held together from the outside with spring clips. Inlet 20 is clipped to the main body 46, holding together impactor plate 12, transition section 28, denuders 14, 16, spacer 34 and spring 36. Bottom section 42 is clipped to main body 46, holding together the filter stages. The clip connectors allow easy assembly and disassembly for the honeycomb denuders and the filters, while assuring that the system is tight enough to prevent leaks.

The impactor is designed to minimize turbulence of the airflow as it passes through the inlet. The ten nozzle configuration (FIG. 1A) spreads the flow around the inlet areas, as well as reducing velocity. The impactor plate ring is positioned to allow equal areas of open space on either side of the ring, and thus equal volumes of air flowing through the different channels through the plate.

The impactor particle collection and loss characteristics were determined experimentally by use of TSI model 3050 vibrating orifice aerosol generator (VOAG, TSI, Inc., St. Paul, Minn.; Berglund and Liu, 1973) and a Aminico Model J4-7439A fluorometer (American Instruments Co., Silver Spring, Md.). The calibration was performed using uranine-tagged oleic acid particles with density equal to 0.914 g/cm$^3$. The particle size using this generation method is accurate to $\pm$2%. The collection efficiency and losses of the impactor were determined as a function of particle size by generating monodisperse particles tagged with uranine dye tracer using the VOAG. Each test consisted of drawing particles generated by the VOAG through the impactor at 10 LPM for a period of 10 to 120 min. The aerosol was monitored using a TSI model 3310 aerodynamic particle sizer (APS, TSI, Inc., St. Paul, Minn.) to verify the monodispersity of aerosols. Afterward the impactor was disassembled and the particles collected on the impaction plate and after filter (Gelman type A/E glass filter) were placed in pyrex beakers with 20 ml 0.001 NaOH buffer. Additional beakers were filled with 20 ml of buffer, and particles that were collected on the interior surfaces were extracted using cotton swabs. The extractions were sonicated for 10 minutes followed by fluorimetric analysis.

The impactor particle collection efficiency and loss curves were determined from the fluorimeter reading normalized with respect to the buffer volumes. The impactor collection efficiency is defined as the mass collected on the interior surfaces of the impaction plate divided by the total mass collected on the impactor. The particle loss is equal to the mass collected on the interior surfaces of the impactor divided by the total.

From the results of the above experiments, the impactor has a cutpoint of 2.06 $\mu$m ($\pm$5%). The sharpness of cut was approximately 1.01 indicating a steep efficiency curve. Particle inlet and internal losses were found to be less than 0.5% for all particle sizes tested.

While designing the sampling system, a major concern was to maintain the flow uniform prior to its entrance into the denuders. Non-uniform flow could result in channelling, with certain areas of the denuder potentially loaded more than others, thus decreasing the capacity of the system. To test for uniformity of the air flow, a filter was placed at various locations downstream from the impactor's plate, and a fluorescent aerosol was passed through the system. Subsequently, the deposition pattern of the fluorescent aerosol was used as a tracer of the flow. The flow was maintained constant at 10 LPM. Transition section 28 was built to smoothly direct the flow from the outer ring of the impactor plate to the inlet to the denuder. From the experimental results it was concluded that uniform distribution of the flow over a cross-section of the system was achieved at a distance equal to one inch downstream the impactor plate. To ensure uniformity, the distance between the impactor plate and the denuder is set at 5.7 cm. When using flows of less than 10 LPM (e.g., 4 and 1.5 LPM), this distance would be even shorter.

The glass honeycomb denuder, shown in FIG. 1C, is a cylinder with a height of 3.8 cm and a diameter of 4.7 cm, containing 212 glass honeycomb tubes, each with a height of 3.8 cm (same height as the denuder) and a inside diameter of 0.2 cm. A thick-walled glass tube with a 47-mm O.D. is filled with the small hexagonal tubes, which are sealed in place using epoxy resin. This design is better than using round small tubes because it leaves less empty space between tubes.

The sample flow through each of the individual tubes, f, is given by the following formula:

$$f = F/n$$

where F is the total flow (in LPM) and n is the number of tubes (212). Assuming that each collision of the analyte on the denuder wall results to its removal from the air sample, the denuder collection efficiency can be determined using the Gormeley-Kennedy equation:

$$E = 1 - \frac{C}{C_o} = 1 - 0.82 \exp\left(-11x \frac{\pi DL}{4f}\right)$$

where E is the collection efficiency (dimensionless), C and $C_o$ are the concentrations of the analyte at exit and entrance of the denuder, D is the gas diffusion coefficient (the diffusion coefficient of nitric acid is 0.12 cm²/s and of ammonia is 0.236 cm²/s), and L is the length of the tube.

The theoretical efficiency of the annular denuders is given by the formula developed by Possanzini et al. (1982):

$$E = 1 - C/C_o$$

$$C/C_o = 0.819 \exp\{-22.53 \, G_a\}$$

where $$G_a = (\pi DL/4F)(d_1 + d_2)/(d_2 - d_1)$$

and wherein
E = collection efficiency
$C/C_o$ = ratio of concentrations exiting and entering the denuder
D = the gas diffusion coefficient in air (cm²/s)
L = length of the annular denuder (21.5 cm)
F = flow rate through the denuders (cm³/s)
$d_1$ = inner diameter of the annulus, 2.20 cm
$d_2$ = outer diameter of the annulus, 2.40 cm Based on the above equations, the theoretical predictions for the collection efficiencies are shown in Table 1.

TABLE 1

Theoretical Efficiencies of Honeycomb and Annular Denuders with Flow of 10 LPM.

| Gas | Diffusion Coefficient (cm²/s) | Honeycomb Denuder | Annular Denuder |
|---|---|---|---|
| $HNO_3$ | 0.121 | 0.999 | 0.999 |
| $NH_3$ | 0.236 | 0.9999 | 0.9999 |

METHOD

The impactor/denuder/filter pack is constructed as follows: The holders for the impactor, denuders, and filter pack are made of machined, anodized aluminum, except for the inside of the nozzles of the multijet impactor, and the mineral oil-coated porous stainless steel ring impactor plate. Those parts exposed to incoming gases are Teflon-coated. The small hexagonal borosilicate glass tubes are sealed inside the larger outer borosilicate glass tube using heat-cured epoxy resin; the sealing process starts with mixing an appropriate curing agent with the liquid epoxy resin. While the mixture remains liquid, the hexagonal tubes are coated and placed inside the larger tube; the epoxy is hardened (cured) by heating the whole system in an oven. After curing, the inside surfaces of the small tubes are sandblasted to create a rough surface which allows the coating to adhere properly. Alternatively, the smaller tubes are sealed inside the outer tube by starting with larger diameters and extruding the ensemble to a smaller size, thereby fusing all the small tubes inside the large tube. Another alternative is to use a ceramic glaze which fuses at a temperature lower than the melting point of borosilicate glass to seal the smaller tubes inside the larger tube.

EXAMPLE 1

HONEYCOMB DENUDER PERFORMANCE EVALUATION

A test system is shown diagrammatically in FIG. 3. Both $NH_3$ and $HNO_3$ were generated by atomizing dilute aqueous nitric acid/ammonia solutions in a Lovelace nebulizer. Both ammonia and nitric acid have high vapor pressures and they are rapidly transported from the aqueous to the vapor phase. This gas generation method has been originally employed by Brauer, et al., 23 Atmospheric Environment 1981 (1989). By varying the concentration of nitric acid or ammonia in the aqueous solution, a wide range of concentrations in the gas phase can be achieved. The air flow to the nebulizer was supplied by one pump, and the pressure was kept constant in all the experiments and equal to 26 psi. The dilution air was provided by another pump, and passed through a series of scrubbers: Purafil (to remove nitrogen oxides and ozone), citric acid coated glass-wool (to remove ammonia), activated charcoal (to remove organics), silica gel (to remove water vapor), and a 0.5 micron filter to remove particles. The humidity of the test atmosphere was controlled by splitting the air flow, passing one air stream through constant temperature Milli-Q water, with a trap to remove excess moisture, and subsequently adjusting the ratio of the dry to humidified air streams. The output of the nebulizer was diluted by the controlled humidity air in a 6 Liters mixing chamber. The flow then entered a sampling manifold. Two pairs of annular denuders and two pairs of honeycomb denuders were connected to the manifold. The sampling flow through each pair was pulled by means of vacuum pumps and was adjusted equal to 10 LPM, by using a Matheson 604 rotameter. Temperature and humidity were monitored by connecting a direct reading probe to the excess flow of the manifold.

After each experiment was completed, all the denuders were extracted with 10 ml of ultra-high purity water and analyzed by ion chromatography. Every analysis series began with a series of five standards. At least three denuders from each batch were used as laboratory blanks.

The collection efficiencies and capacities for nitric acid and ammonia have been determined as a function of humidity, sampling time, coating solution composition and analyte concentration. In each experiment, the efficiency, precision and capacity of the honeycomb denuders have been compared to those of the annular denuders. The capacity test is necessary, especially for applications in long-duration integrated sampling. The capacity of the denuder is defined as the maximum amount of gas that can be collected without any significant decrease (about 5%) in the collection efficiency. The amount of gas collected (gas concentration × sampling flow rate × sampling time), expressed in mg was plotted versus the honeycomb and the annular denuder's efficiency, for nitric acid and ammonia respectively. For nitric acid, the capacity of the honeycomb denuder was about 10 mg (compared to 4 mg for the annular denuder). In the case of the annular denuder, a sharp decrease in the efficiency occurs when the amount collected exceeded 6 mg. The honeycomb denuder can collect at least 1.2 mg of ammonia without a detectable decrease in its efficiency, while the efficiency of the annular denuder decreases sharply when the total collection exceeds 0.3 mg.

Table 2 shows the collection efficiency for nitric acid and ammonia as a function of sampling time and relative humidity. The reported values for both annular and honeycomb denuder are averages of duplicate measurements. In these experiments, sampling was conducted simultaneously, using both the annular and the honeycomb denuders from the same manifold. The collection efficiency of a denuder was determined by dividing the amount of gas collected on the first denuder by the sum of the amounts collected on the first and the second denuder.

The coating solution was the same for both types of denuders. It can be seen that for low concentrations and sampling times, the efficiencies of both types of denuders are similar and reasonably close to the theoretically predicted efficiency of 0.999. As the amount of the nitric acid collected increases, the efficiency of the annular denuder falls rapidly. In addition, the results suggest that the efficiency of the annular denuder decreases as the gas collection exceeds 7 mg, whereas no detectable decrease in the efficiency of the honeycomb denuder was observed, even at total nitric acid collection equal to 10 mg. This is expected, since the surface area of the honeycomb denuder is approximately 507.5 $cm^2$, whereas the total surface area of the annular denuder is 310.7 $cm^2$, therefore its capacity should be smaller than the honeycomb denuder.

TABLE 2

Nitric Acid Collection Efficiency Test.
Comparison Between Honeycombs and Annular Denuders.

| Sampl. Time (hrs.) | R.H (%) | 1st Annular Denuder (ppb) | 2nd Annular Denuder (ppb) | Efficiency of Annular Denuder (%) | 1st Honeycomb Denuder (ppb) | 2nd Honeycomb Denuder (ppb) | Efficiency of Honeycomb Denuder (%) |
|---|---|---|---|---|---|---|---|
| 3  | 20 | 38.2  | 0.70  | 98.2 | 36.3  | 1.20 | 97.3 |
| 3  | 50 | 228.2 | 0.28  | 99.9 | 248.3 | 1.55 | 99.6 |
| 3  | 90 | 221.0 | 0.45  | 99.8 | 221.4 | 0.90 | 99.6 |
| 8  | 20 | 51.5  | 0.70  | 98.7 | 46.2  | 1.40 | 97.0 |
| 15 | 50 | 148.9 | 8.60  | 94.0 | 124.1 | 0.47 | 99.7 |
| 16 | 20 | 162.7 | 0.48  | 99.7 | 159.5 | 2.37 | 98.5 |
| 24 | 20 | 155.3 | 5.76  | 96.4 | 158.6 | 1.44 | 99.1 |
| 24 | 80 | 184.9 | 56.10 | 76.8 | 255.5 | 4.80 | 98.2 |

Used Coating Solution: 1% $Na_2CO_3$: 1% glycerol for both types of denuders.

Table 3 shows the collection efficiency of honeycomb denuders for nitric acid for two different coating solution compositions, with different sampling times, and relative humidities. Simultaneous sampling was done as above. Since the collection efficiency is already high for both denuders, the difference may not appear to be significant. However, it is evident from the experimental results, that the 2% $Na_2CO_3$:1% Glycerol in 1:1 water/methanol solution slightly improves the performance characteristics of the honeycomb denuder, compared to the 1% $Na_2CO_3$:1% Glycerol in 1:1 water/methanol solution.

TABLE 3

Nitric Acid Collection Efficiency Test.
Comparison Between Honeycomb Denuders with Different Coating Solutions.

| Sampltime (hrs.) | R.H (%) | 1st Honeycomb Denuder A (ppb) | 2nd Honeycomb Denuder A (ppb) | Efficiency of Denuder A (ppb) | 1st Honeycomb Denuder B (ppb) | 2nd Honeycomb Denuder B (ppb) | Efficiency of Denuder B (%) |
|---|---|---|---|---|---|---|---|
| 3  | 20 | 39.1  | 1.00 | 97.6 | 36.3  | 1.2 | 97.3 |
| 3  | 50 | 246.0 | 0.7  | 99.8 | 248.3 | 1.6 | 99.6 |
| 3  | 90 | 221.0 | 0.5  | 99.8 | 221.4 | 0.9 | 99.6 |
| 8  | 20 | 50.7  | 0.9  | 98.3 | 46.2  | 1.4 | 97.0 |
| 15 | 50 | 119.4 | 0.3  | 99.8 | 124.1 | 0.5 | 99.7 |
| 16 | 20 | 161.8 | 2.5  | 98.5 | 159.5 | 2.4 | 98.5 |
| 24 | 20 | 172.0 | 0.5  | 99.7 | 158.6 | 1.4 | 99.1 |

TABLE 3-continued

Nitric Acid Collection Efficiency Test.
Comparison Between Honeycomb Denuders with Different
Coating Solutions.

| Sampltime (hrs.) | R.H (%) | 1st Honeycomb Denuder A (ppb) | 2nd Honeycomb Denuder A (ppb) | Efficiency of Denuder A (%) | 1st Honeycomb Denuder B (ppb) | 2nd Honeycomb Denuder B (ppb) | Efficiency of Denuder B (%) |
|---|---|---|---|---|---|---|---|
| 24 | 80 | 271.9 | 0.8 | 99.7 | 255.5 | 4.8 | 98.2 |

Used Coating Solution: 2% Na$_2$CO$_3$: 1% glycerol for Denuder A; 1% Na$_2$CO$_3$: 1% glycerol for Denuder B.

Analysis of blank denuders indicated that there were no detectable amounts of nitric acid. HNO$_3$ concentrations were determined from linear regression equations for NO$_3^-$ standards (Koutrakis, et al., 22(1) *Atmospheric Environment* 157 (1988)).

Table 4 compares the ammonia collection efficiencies of annular and honeycomb denuders. The total amount of ammonia collected on the first annular and honeycomb denuder is also included. In this case, the coating solution was the same for both types of denuders (2% citric acid, 1% glycerol in methanol). The efficiencies of the honeycomb denuder and the annular denuder are similar for low NH$_3$ concentrations and sampling durations. However, as either the NH$_3$ concentration exceeds 200 ppb or the collected exceeds 0.31 mg, the collection efficiency of the annular denuder falls rapidly. As it can be seen, in Table 4, the efficiency of the honeycomb denuder does not detectably decrease until an amount of 1.2 mg is exceeded. NH$_3$ concentrations were determined from cubic regression equations of NH$_4^+$ standards, as above.

TABLE 4

Ammonia Collection Efficiency Tests.
Comparison Between Honeycomb and Annular Denuders.

| Sampl. Time (hrs.) | R.H (%) | 1st Honey-comb Denuder (ppb) | 2nd Honey-comb Denuder (ppb) | Collection Efficiency of Denuder (%) | 1st Annular Denuder (ppb) | 2nd Annular Denuder (ppb) | Collection Efficiency of Annular Denuder (%) |
|---|---|---|---|---|---|---|---|
| 3 | 20 | 361.5 | 20.1 | 94.7 | 210.3 | 177.0 | 54.3 |
| 3 | 50 | 144.1 | 4.0 | 97.3 | 148.5 | 3.3 | 97.8 |
| 4 | 85 | 277.7 | 3.0 | 99.0 | 169.7 | 111.7 | 60.3 |
| 6 | 50 | 233.7 | 8.8 | 96.4 | 137.2 | 107.4 | 56.1 |
| 18 | 20 | 77.3 | 0.6 | 99.3 | 78.8 | 0.7 | 99.0 |
| 18 | 85 | 322.3 | 137.3 | 70.1 | 237.5 | 170.6 | 58.2 |
| 19 | 50 | 147.9 | 1.8 | 98.8 | 97.2 | 53.9 | 64.3 |
| 24 | 85 | 65.9 | 0.3 | 99.5 | 70.4 | 0.3 | 99.6 |
| 24 | 20 | 18.8 | 0.3 | 99.6 | 18.0 | 0.3 | 99.5 |

The results for both nitric acid and ammonia show that there is no evidence that the collection efficiencies are dependent on the relative humidity. This is in agreement with the results obtained from Brauer et al., 23 *Atmospheric Environment* 1981 (1989), who studied the effects of humidity on the collection efficiency of annular denuders. In addition, it can be seen that the performance of the honeycomb denuder at gas concentrations much higher than those in typical polluted environments is excellent. For both nitric acid and ammonia collection, the capacity of the honeycomb denuder is larger than the capacity of the annular denuder, since the collection surface of the honeycomb is larger.

The precision is HNO$_3$ and NH$_3$ measurements is presented in Table 5. The mean relative standard deviation for nitric acid was found to be 5.5%, while the mean relative standard deviation for ammonia was found to be 3.0.

TABLE 5

Precision for HNO$_3$ and NH$_3$ Measurements Using the Honeycomb Denuders.

| | HNO$_3$ | | | |
|---|---|---|---|---|
| Experiment | Mean Concentration (ppb) | % RSD | Mean Concentration (ppb) | % RSD |
| I | 163.6 | 5.1 | 77.3 | 5.3 |
| II | 253.7 | 6.3 | 144.1 | 1.1 |
| III | 38.0 | 2.9 | 147.9 | 2.4 |
| IV | 237.8 | 4.9 | 233.7 | 0.7 |
| V | 50.9 | 3.6 | 277.7 | 1.5 |
| VI | 145.3 | 12.7 | 322.3 | 6.8 |
| VII | 163.1 | 7.9 | 65.9 | 2.9 |
| VIII | 221.6 | 0.9 | 19.2 | 3.7 |

% RSD is the percent standard deviation.

EXAMPLE 2

PARTICLE LOSS

The purpose of this example is to examine particle losses in the size range 0.05 to 2.0 microns through 2.54 cm long glass honeycomb denuders, similar to those in Example 1, used in series.

The measurements were made with fluorescent monodisperse latex particles for three different sampling flow rates. In addition the effect of relative humidity and the denuder surface coating on the transmission characteristics was examined.

The theoretical predictions for particle losses in the size range 0.1-2.0 μm due to diffusion only are in the range 0.1-2% (Hinds, *Aerosol Technology: Properties, Behavior and Measurement of Airborne Particles*, John Wiley & Sons, New York (1982). Since the uncertainty caused by fluctuations in the particle concentration of aerosol generated by most conventional generators is in the order of at least 1%, the use of a highly sensitive method such as fluorescence analysis was considered necessary for measuring such small losses.

FIG. 4 shows the experimental setup used for the evaluation of the particle losses through the honeycomb denuders. Suspensions of 2.5% by weight yellow-green latex microspheres (Fluoresbrite, Polysciences, warrington, Pa.) were nebulized by a pocket nebulizer (Retec X-70/N) using room air at 20 psi as described by Zeltner, et al., 54 *J. Applied Physiology* 1137 (1991). The volumetric flow rate of the nebulizer was estimated to be approximately 5.5 LPM and the output concentration was approximately 0.25 cc/minute. The nebulizer was connected to a syringe pump in order to atomize large amounts (120 ml) of the fluorescent solution, and also to ensure a stable atomization process. Seven different particle sizes were used: 0.06, 0.15, 0.23, 0.46, 0.77, 1.1. and 2.0 μm in diameter. The particle size range was selected based on the results of previous ambient sampling studies of acid aerosols. These studies showed that the size of atmospheric sulfate particles varies from 0.2 to 1.0 μm with an average around 0.5 μm depending on the relative humidity. The aerosol was subsequently dried in a 6-liter dry-air dilution chamber and passed through a 1-liter chamber where four Polonium 210 ionizing units were placed (Staticmaster, NRD Inc.) to neutralize any particle charge. After neutralization, the aerosol was passed through the test system (FIG. 4) which consisted of an inlet, one 25 cm elutriator tube (inner diameter 4.7 cm), two 2.54 cm long glass honeycomb denuders separated by a 2.54 cm long spacer, and a 47 mm glass fiber filter placed downstream of the denuders to collect the remaining particles. The aerosol passed through the test system at a known flow rate (1.5, 4 and 10 LPM) measured with a rotameter. The test system was positioned vertically to minimize gravitational losses. Another part of the test aerosol was passed through an optical particle size analyzer (model LAS-X Particle Measuring System, Inc., Boulder, Colo.) which recorded the particle size distribution throughout the experiment at a sampling flow rate of 1.5 LPM. The PMS laser spectrometer had been calibrated prior to the experiments using polystyrene latex particles (Polysciences, Warrington, Pa.). In every experiment the optical size analyzer confirmed that >95% of the particles were singlets. Since the detection limit of this particular PMS model was 0.09 μm, particles 0.06 μm in diameter could not be measured. Nevertheless, when the test aerosol consisted of 0.06 μm particles, the PMS showed only very few particles in the size range of 0.09-0.15 μm. This was taken as an indirect confirmation of the particle size of the generated aerosol. The only reason that particles as small as 0.06 μm were used was to extend the diffusion losses to somewhat larger values than 1% (which is the theoretical prediction for particles larger than 0.1 μm). Finally, the relative humidity was controlled by adjusting the flow rate of the dry dilution air and was monitored with a direct-reading probe.

After a sufficient amount of the aqueous fluorescent suspension was nebulized, the two denuders, the elutriator, and the spacer were washed separately with 10 ml of ethyl acetate, as recommended by the manufacturer. Every experiment lasted approximately two hours. The longer duration of the experimental procedure that should have been necessary for accurate loss determinations for smaller flow rates (1.5 LPM) was compensated for by the higher diffusion losses. Finally, the glass fiber filter was extracted using 20 ml of ethyl acetate. Subsequently, the filter and the solution were ultrasonicated for a few minutes to ensure that all particles were transferred from the filter to the extraction solution. The solution was filtered through a new 1.0 μm Nucleopore filter to remove glass fibers dislodged during the sonication. The quantities of the fluorescent dye in the extraction solutions were measured by a fluorometer (FD-300 Fluorescence Detector, GTI, Concord, Mass.) to determine particle concentration. Linear regression analysis was performed for standards ranging from zero (Ethyl acetate solution) to 50 μg of PSL particles/ml ethyl acetate. In addition, in every experiment the fluorometer was calibrated by consecutively diluting the total amount collected on the filter and recording the indication of the instrument until loss of linearity between the solution concentration and the instrument's indication was detected. The method can detect as little as 100 μg of PSL particles in 1 ml solution and it is linear up to about 25 mg of particles in 1 ml of ethyl acetate solvent. Samples were collected for approximately 2 hours so that a detectable amount of fluorescence would be collected.

Results from the experiments are summarized in Tables 6-8. Each experimental value is the average of at least two experiments. In each experiment the amount of fluorescent particles lost in the elutriator, denuders, spacer and filter was determined. In all experiments the total amount in the spacer and the elutriator was found to be comparable to the lowest detection limit of the fluorometer (about 0.05% of particles).

TABLE 6

Particle Loss Through Honeycomb Denuders at 60-70% R.H.

| Particle Diameter (microns) | Relative Humidity (%) | (%) Loss at 1.5 LPM | (%) Loss at 4 LPM | (%) Loss at 10 LPM |
| --- | --- | --- | --- | --- |
| 0.06 | 65 | 4.20 (±0.90) | 2.30 (±0.25) | 1.75 (±0.20) |
| 0.15 | 70 | 1.75 (±0.20) | 0.65 (±0.05) | 0.40 (±0.05) |
| 0.23 | 70 | 1.20 (±0.20) | 0.60 (±0.10) | 0.36 (±0.05) |
| 0.46 | 75 | 1.40 (±0.10) | 0.46 (±0.05) | 0.27 (±0.05) |
| 0.77 | 65 | 0.40 (±0.05) | 0.28 (±0.05) | 0.21 (±0.05) |
| 1.1 | 70 | 0.80 (±0.10) | 0.40 (±0.05) | 0.33 (±0.07) |
| 2.0 | 60 | 1.10 (±0.20) | 1.30 (±0.20) | 1.80 (±0.20) |

1. Particles losses are averages of at least two runs.
2. The denuders were used without any coating.
3. Numbers in parentheses are standard deviations based on duplicate measurements.

Table 6 shows the experimental data for particle loss in the honeycomb denuders for various particle sizes and sampling flow rates at a relative humidity range of 60-70%. The denuders were uncoated. In the following discussion, the experimental data for various flow rates is compared to theoretical losses by diffusion in laminar flows. The flow through the hexagonal cells of the honeycomb denuders was assumed to be equivalent to the flow through small tubes with diameter equal to 0.2 cm. The Reynolds number at 10 LPM based on the cell side was about 30, therefore the flow was assumed to be laminar. The diffusion loss ($\eta_L$) in a tube of an aerosol flowing through are given by the following equations (Gormley and Kennedy, 1949):

$$\eta_L = 1 - C_{out}/C_e \qquad (1)$$

where:
$C_{out}$ is the concentration of aerosol after the tube
$C_e$ is the concentration of aerosol at the entrance to the tube $$\eta_L = 3.77\mu - 5.50\mu^{2/3} \qquad (2)$$
(for $\mu < 0.007$)

-continued $$N_L = 1 - 0.819\exp(-11.5\mu) + \quad (3)$$
$$0.0975\exp(-70.1\mu) + 0.0325\exp(-179\mu)$$
(for $\mu > 0.007$)

$$\mu = \frac{DL}{Q_n} \quad (4)$$

where:
D is the particle diffusion coefficient (cm²/s)
L is the length of the tube (2.54 cm)
$Q_n$ is the flow rate through the individual tubes of the honeycomb denuders (equal to the total flow rate divided by the total number of the denuder cells, 212 in this case)

When more than one denuder is connected in series, the losses of the previous stage have to be taken into account when determining the loss through the next denuder. For n stages the cumulative loss is:

$$\eta = 1 - (1-\eta)^n \quad (5)$$

Nevertheless, as it can be seen from the results presented in Table 6, the particle loss through the honeycomb denuders in the size range 0.1–2.0 μm are so small (2% or loss) that the overall loss can be taken practically equal to the sum of the individual losses through the denuders. Only in the case of 0.05 μm particles at 1.5 LPM the diffusion loss per denuder becomes significant (5%) thus the losses in the previous stage need to be taken into account. The experiments suggested that the losses in two honeycomb denuders connected in series were practically identical. The experimental losses appear to have similar trends with the predictions of the diffusion theory. For all flow rates the losses are higher than the theoretical predictions, especially for the 0.06 μm particles. It is quite possible that some of the particles carried charges despite the fact that the generated aerosol passed through a neutralizer. In addition, the diffusion theory does not account for entrance effects occurring when the aerosol sample enters abruptly from a tube of 4.7 cm diameter into the 2 mm cells of the honeycomb denuders. The abrupt contraction of the cross-sectional area of the flow induces turbulence in the transition area with a subsequent increase in the particle losses.

A minimum level of particle loss occurs at 0.77 μm at all sampling flow rates. As the particle diameter becomes larger than 0.77 μm the loss through the honeycomb denuders increases and cannot be explained by the diffusion theory only. The particles flow through a 25 cm long elutriator prior to entering the first honeycomb denuder. As it was previously stated in the description of the sampler, the particle concentration becomes uniform across the diameter of the elutriator. The total area of the honeycomb denuder is 17.34 cm² and the total cross sectional area of the hexagonal cells is 6.66 cm². Therefore, there is a lot of surface area between the honeycomb cells which may serve as deposition site for particles of non-negligible inertia, such as particles larger than 1 micron. The particles may be captured by the denuder front surface by impaction and interception. This assumption can be further sustained by the fact that the particle loss for particles larger than 1 micron is much larger than the prediction by diffusion at 10 LPM than at 1.5 LPM. Table 6 shows that the diffusion losses of 2 μm particles at 1.5 LPM ar 1.1% while at 10 LPM the losses become 1.8%. If losses where due only to diffusion they should be higher at the lower flow rate.

TABLE 7

Particle loss in honeycomb denuders at 35–45% R.H. and 1.5 LPM sampling flow rate.

| Particle diameter (microns) | Relative Humidity (%) | (%) Loss |
|---|---|---|
| 0.06 | 35 | 3.80 (±0.40) |
| 0.15 | 45 | 1.50 (±0.15) |
| 0.23 | 40 | 1.00 (±0.10) |
| 0.46 | 35 | 1.20 (±0.20) |
| 0.77 | 40 | 0.35 (±0.05) |
| 1.1 | 35 | 1.10 (±0.10) |
| 2.0 | 35 | 1.70 (±0.15) |

1. Particle losses in this table are averages of at least two runs. In each run a pair denuders in series has been tested.
2. The denuders were used without any coating.
3. The numbers in the parentheses are standard deviations based on duplicate measurements.

Table 7 shows the results of the particle loss tests conducted at a lower relative humidity range (30–45%). The theory of diffusion predicts that particle losses are higher at 1.5 LPM, therefore tests were only conducted at this flow rate to examine the effect of the relative humidity on particle deposition. It is believed that charge effects and electrostatic deposition are enhanced at lower humidities (Zimon, *Adhesion of Dust and Powder* 1980, Dahneke, 40 *J. Colloid Interface Sci.* 1 (1971)). Particle deposition did not appear to be significantly different as the humidity decreased. The electrostatic effect might have been more pronounced at even lower humidities (10–20%).

A previous study (Ye, et al., 14 *Aerosol Science and Technology* 102 (1991)) has demonstrated that the particle loss in annular denuders decreases significantly when the surface of the denuders is coated. This has been attributed to the decrease of electrostatic forces that are developed between particles and the denuder surface. A coating solution of 2% citric acid: 1% glycerol in methanol was prepared and the glass honeycomb denuders were coated and dried according to the procedure described by Koutrakis, et al., 22 *Environmental Science and Technology* 1463 (1988).

TABLE 8

Particle loss for honeycomb denuders coated with citric acid at 1.5 LPM sampling flow rate.

| Particle diameter (microns) | (%) Loss Citric acid | (%) Loss No Coating |
|---|---|---|
| 0.06 | 2.40 (±0.20) | 4.20 (±0.90) |
| 0.15 | 1.10 (±0.10) | 1.75 (±0.20) |
| 0.23 | 0.95 (±0.10) | 1.20 (±0.20) |
| 0.46 | 0.58 (±0.07) | 1.40 (±0.10) |
| 0.77 | 0.43 (±0.08) | 0.40 (±0.05) |
| 2.0 | 2.35 (±0.15) | 1.80 (±0.20) |

1. Particle losses in this table are averages of at least two runs. In each run a pair denuders in series has been tested.
2. The denuders were used without any coating.
3. The numbers in the parentheses are standard deviations based on duplicate measurements.

Table 8 shows the results of the comparison tests for particle losses between coated and uncoated denuders. The sampling flow rate was 1.5 LPM in order to increase the sensitivity of the experiments. Although particle losses are very small in both cases, losses in coated denuders were consistently smaller than the losses in uncoated denuders for particles smaller than 0.77 μm in diameter. This conclusion is in agreement with previous investigations. Thus, coating the denuders did not decrease the losses of particles larger than 1.0 μm. This suggests that the deviation from the theory of diffusion in this particle size range is due to inertial rather than electrostatic deposition mechanisms.

Other embodiments are within the following claims.

We claim:

1. A denuder for collection of gases, comprising a plurality of generally parallel elongated tubes having a surface formed from an inert non-metallic material, said tubes being configured and arranged to allow recovery of gaseous material collected on each said surface.

2. The denuder of claim 1, wherein said material is selected from the group consisting of: glass, ceramic, and plastic.

3. The denuder of claim 2, wherein said plastic is a resin.

4. The denuder of claim 1, wherein at least 20 said tubes are provided.

5. The denuder of claim 1, wherein at least 50 said tubes are provided.

6. The denuder of claim 1, wherein at least 100 said tubes are provided.

7. The denuder of claim 1, wherein said tubes have a hexagonal cross-section.

8. The denuder of claim 1, wherein said tubes have an circular cross-section.

9. The denuder of claim 1, wherein said denuder has a length less than 5 cm and a width less than 6 cm.

10. A gas collection system, comprising
a denuder for collection of gases, comprising a plurality of generally parallel elongated tubes having a surface formed from an inert non-metallic material said tubes being configured and arranged to allow recovery of gaseous material collected on each said surface,
a gas inlet nozzle configured and arranged to allow gas to enter said system and pass through said denuder, and
an impactor plate configured and arranged to collect particles in said gas which pass through said nozzle.

11. The system of claim 10, wherein said nozzle and impactor plate are configured and arranged to cause particles of size greater than 2.5 μm to contact said plate.

12. The system of claim 10, wherein said nozzle comprises a circular array of apertures.

13. The system of claim 10, comprising a plurality of said denuders.

14. The system of claim 13, wherein one said denuder is adapted for collection of acid gases.

15. The system of claim 13, wherein one said denuder is adapted for collection of basic gases.

16. The system of claim 10 or 13, further comprising a filter pack configured and arranged to collect particles not collected on said impactor plate.

17. The system of claim 16, wherein said filter pack comprises a first teflon filter.

18. The system of claim 17, wherein said filter pack comprises a second glass fiber filter coated to collect acid or basic gases.

19. A method for sampling gas comprising a denuder for collection of gases, said denuder comprising a plurality of generally parallel elongated tubes having a surface formed from an inert non-metallic material, said tubes being configured and arranged to allow recovery of gaseous material collected on each said surface.

* * * * *